US012673050B2

(12) United States Patent
Ramsden et al.

(10) Patent No.: US 12,673,050 B2
(45) Date of Patent: Jul. 7, 2026

(54) COMPOSITIONS AND THEIR USE FOR THE TREATMENT OF A1-ANTITRYPSIN DEFICIENCY

(71) Applicant: Centessa Pharmaceuticals (UK) Limited, Altrincham (GB)

(72) Inventors: Nigel Ramsden, Babraham (GB); David John Fox, Babraham (GB); James Andrew Huntington, Altrincham (GB)

(73) Assignee: CENTESSA PHARMACEUTICALS (UK) LIMITED, Altrincham (GB)

( * ) Notice: Subject to any disclaimer, the term of this patent is extended or adjusted under 35 U.S.C. 154(b) by 395 days.

(21) Appl. No.: 18/540,695

(22) Filed: Dec. 14, 2023

(65) Prior Publication Data

US 2024/0197707 A1 Jun. 20, 2024

Related U.S. Application Data

(63) Continuation of application No. PCT/GB2022/051502, filed on Jun. 15, 2022.

(30) Foreign Application Priority Data

Jun. 15, 2021 (GB) ..................................... 2108523

(51) Int. Cl.
*A61K 31/445* (2006.01)
*A61P 43/00* (2006.01)

(52) U.S. Cl.
CPC ............ *A61K 31/445* (2013.01); *A61P 43/00* (2018.01)

(58) Field of Classification Search
None
See application file for complete search history.

(56) References Cited

U.S. PATENT DOCUMENTS

| | | | |
|---|---|---|---|
| 8,436,013 | B2 | 5/2013 | Liu et al. |
| 9,084,782 | B2 | 7/2015 | Kwon et al. |
| 2011/0065707 | A1 | 3/2011 | Ackermann et al. |
| 2020/0361939 | A1 | 11/2020 | Bandarage et al. |
| 2023/0089087 | A1 | 3/2023 | Ramsden et al. |

FOREIGN PATENT DOCUMENTS

| | | | |
|---|---|---|---|
| EP | 0520336 | A2 | 12/1992 |
| JP | H05345753 | A | 12/1993 |
| JP | 2007538106 | A | 12/2007 |
| JP | 2013504544 | A | 2/2013 |
| WO | WO-2005113542 | A2 | 12/2005 |
| WO | WO-2008143633 | A2 | 11/2008 |
| WO | WO-2011029808 | A1 | 3/2011 |
| WO | WO-2011110852 | A1 | 9/2011 |
| WO | WO-2018104220 | A1 | 6/2018 |
| WO | WO-2019243841 | A1 | 12/2019 |
| WO | WO-2020081257 | A1 | 4/2020 |
| WO | WO-2021116703 | A1 | 6/2021 |
| WO | WO-2022263816 | A1 | 12/2022 |

OTHER PUBLICATIONS

Chemical Abstracts Service. CAS Registry: 1786870-80-1. STN Entry Date Jun. 23, 2015.
Chemical Abstracts Service. CAS Registry: 2649795-64-0. STN Entry Date Jul. 6, 2021.
Chemical Abstracts Service. CAS Registry: 727983-32-6. STN Entry Date Aug. 18, 2004.
Chemical Abstracts Service. CAS Registry: 891392-15-7. STN Entry Date Jul. 10, 2006.
Berthelier et al., "Discovery Of An Inhibitor Of Z-Alpha1 Antitrypsin Polymerization," PLoS One 10(5)(e0126256):1-18 (May 11, 2015).
Bouchecareilh et al., Histone deacetylase inhibitor (HDACi) suberoylanilide hydroxamic acid (SAHA)-mediated correction of α1-antitrypsin deficiency. The Journal of biological chemistry 287(45):38265-38278 (2012).
Burrows et al., "Chemical Chaperones Mediate Increased Secretion Of Mutant α1-Antitrypsin (α1-AT) Z: A Potential Pharmacological Strategy For Prevention Of Liver Injury And Emphysema In α1-AT Deficiency," Proceedings of the National Academy of Sciences of the United States of America 97(4):1796-1801 (Feb. 15, 2000).
Carlson et al., "Accumulation of PiZ Alpha 1-Antitrypsin Causes Liver Damage In Transgenic Mice," The Journal of Clinical Investigation 83(4):1183-1190 (1989).
Certified GB1918410.0, filed Dec. 13, 2019.
Chang et al., "Small-Molecule Peptides Inhibit Z α1-Antitrypsin Polymerization," Journal of Cellular and Molecular Medicine 13(8B):2304-2316 (2009).
Corral et al., "Exploiting The Evolutionary Relationship Between Malarial Parasites And Plants To Develop New Herbicides," Angewandte Chemie International Edition English 56(33):9881-9885 (Jul. 12, 2017).
Database accession No. 1394768-24-1, Chemical Abstracts Service (Sep. 18, 2012).
Database Accession No. 1786658-64-7, Registry, Chemical Abstracts Service, Columbus, Ohio, US, 01 Page (Jun. 23, 2015), XP002801653.
Database Accession No. 1786746-43-7, Registry, Chemical Abstracts Service, Columbus, Ohio, US, 01 Page (Jun. 23, 2015), XP002801660.
Database accession No. 1840546-43-1, Chemical Abstracts Service (Jan. 3, 2016).
Database accession No. 727717-69-3, Chemical Abstracts Service (Aug. 17, 2004).
Database accession No. 891392-68-0, Chemical Abstracts Service (Jul. 10, 2006).

(Continued)

*Primary Examiner* — Samantha L Shterengarts
(74) *Attorney, Agent, or Firm* — WILSON SONSINI GOODRICH & ROSATI

(57) ABSTRACT

The invention relates to pharmaceutical compositions comprising (S)-1-(2-(trifluoromethyl)phenyl)sulfonyl)piperidine-3-carboxylic acid and their medical use, for example for use in the treatment of $\alpha_1$-antitrypsin deficiency (AATD).

9 Claims, 4 Drawing Sheets

(56) References Cited

OTHER PUBLICATIONS

Figure 1:
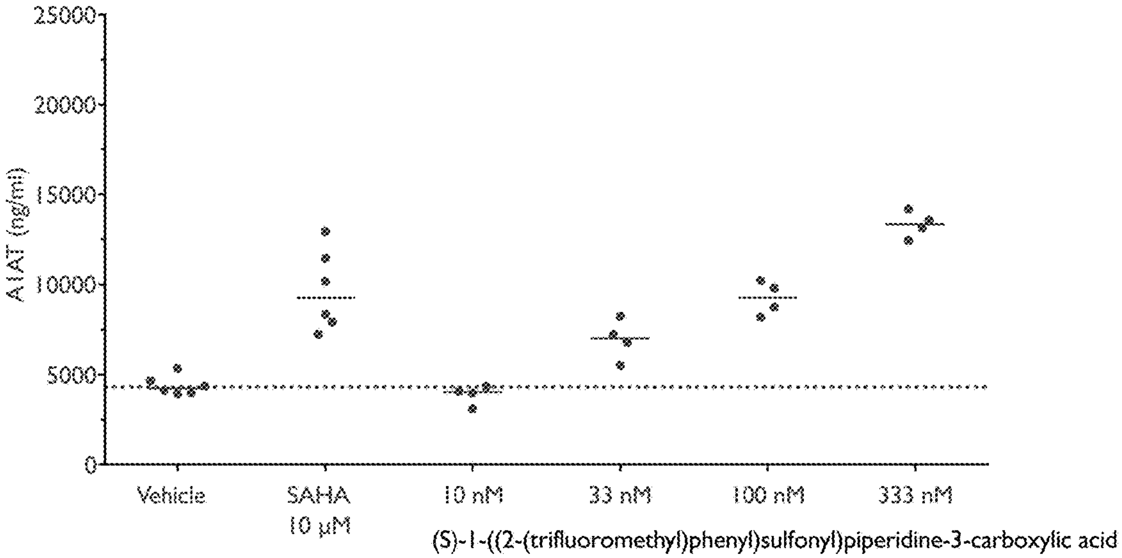

Dycaico et al., "Neonatal Hepatitis Induced by Alpha 1-Antitrypsin: A Transgenic Mouse Model," Science 242(4884):1409-1412 (Dec. 9, 1988).
Elkins et al., "Variability in High-throughput Ion-Channel Screening Data and Consequences for Cardiac Safety Assessment," Journal of Pharmacological and Toxicological Methods 68:112-122 (2013).
Elliott et al., "Topography of a 2.0 A Structure of Alpha1-Antitrypsin Reveals Targets for Rational Drug Design to Prevent Conformational Disease," Protein Science 9:1274-1281 (2000).
GB1918410.0 Search Report dated Jun. 10, 2020.
Gould. Salt Selection for Basic Drugs. International Journal of Pharmaceutics, Elsevier, Biomedical Division, NL 33(1-3):201-217 (1986) Retrieved on Nov. 1, 1986].
Guidance for Industry. Estimating the Maximum Safe Starting Dose in Initial Clinical Trials for Therapeutics in Adult Healthy Volunteers, U.S. Department of Health and Human Services-FDA, Jul. 2005, Retrieved from the Internet: http://www.fda.gov/cder/guidance/index.html.
Huntington "How And Why The Z Variant Of α1-Antitrypsin Polymerises, And What Can Be Done About It," 7th International Symposium On Serpin Biology, Structure And Function, Powerpoint Presentation, 34 Pages (Apr. 1, 2014).
Knaupp et al., "Kinetic Instability of the Serpin Z Alpha1-Antitrypsin Promotes Aggregation," Journal of Molecular Biology 396:375-383 (2010) (Available Online on Nov. 26, 2009).
Mallya, Meera, et al., Small Molecules Block The Polymerization Of Z Alpha1-antitrypsin And Increase The Clearance Of Intracellular Aggregates. Journal of Medicinal Chemistry 50(22):5357-5363 (2007).
Parfrey et al., "Targeting a Surface Cavity of Alpha 1-Antitrypsin to Prevent Conformational Disease," The Journal of Biological Chemistry 278(35):33060-33066 (Aug. 29, 2003).
PCT/GB2020/053187 International Search Report and Written Opinion dated Feb. 1, 2021.
PCT/GB2022/051502 International Search Report and Written Opinion dated Aug. 17, 2022.
Reddy et al., "Synthesis And Antimicrobial Screening Of Some New Piperidine Derivatives," Journal of Applicable Chemistry 2(6):1501-1508 (2013).
Registry, Chemical Abstracts Service, Columbus, Ohio, US, Database accession No. 1787438-88-3 (Jun. 24, 2015), XP002801654.
Registry, Chemical Abstracts Service, Columbus, Ohio, US, Database accession No. 630049-57-9, (Dec. 23, 2003), XP002801655.
Seyama et al., "Siiyama (Serine 53 (TCC) to Phenylalanine 53 (TTC)). A New Alpha 1-Antitrypsin-Deficient Variant with Mutation on a Predicted Conserved Residue of the Serpin Backbone," The Journal of Biological Chemistry 266(19):12627-12632 (Jul. 5, 1991).
Weaver et al., "Cytochrome P450 Inhibition Using Recombinant Proteins And Mass Spectrometry/multiple Reaction Monitoring Technology In A Cassette Incubation," Drug Metabolism and Disposition 31(7):955-966 (2003).

COMPOSITIONS AND THEIR USE FOR THE TREATMENT OF A1-ANTITRYPSIN DEFICIENCY

CROSS-REFERENCE TO RELATED APPLICATIONS

This application is a continuation of International Application No. PCT/GB2022/051502, filed Jun. 15, 2022, which is incorporated herein by reference in its entirety.

BACKGROUND OF THE INVENTION

The invention relates to pharmaceutical compositions comprising (S)-1-((2-(trifluoromethyl)phenyl)sulfonyl)piperidine-3-carboxylic acid and their medical use.

$\alpha_1$-Antitrypsin (A1AT) is a member of the serpin superfamily produced by the liver and secreted into the blood. It inhibits a variety of serine proteases, especially neutrophil elastase. When blood levels of A1AT are low, excessive neutrophil elastase activity degrades lung tissue resulting in respiratory complications, such as chronic obstructive pulmonary disease (COPD).

The reference range of A1AT in blood is 0.9-2.3 g/L. Levels lower than this are typical of $\alpha_1$-antitrypsin deficiency (A1AD or AATD), a genetic disorder caused by mutations in the SERPINA1 gene, coding for A1AT. The Z mutation, the most common cause of AATD, is the substitution of glutamate to lysine at position 366 of A1AT (UniProtKB—P01009 (A1AT_HUMAN)), corresponding to position 342 in the mature protein (Z A1AT). The Z mutation affects the folding of A1AT resulting in only a small fraction acquiring the native/active state. The remainder is either cleared as misfolded protein or accumulates in the liver as stable polymers. As a consequence of the misfolding, homozygous carriers of the Z mutation (ZZ) have plasma levels of A1AT that are 10-15% of normal, predisposing carriers to COPD. Accumulation of Z ALAT polymers in liver cells predisposes carriers to cirrhosis, liver cancer and other liver pathologies.

The current treatment for the lung manifestation of AATD involves augmentation therapy using A1AT concentrates prepared from the plasma of blood donors. The US FDA has approved the use of four A1AT products: Prolastin, Zemaira, Glassia, and Aralast. Dosing is via once weekly intravenous infusion. Augmentation therapy has been demonstrated to slow progression of COPD. The liver manifestations of AATD (e.g. cirrhosis and cancer) are treated with steroids and liver transplantation. Investigational approaches to improved treatment of the liver manifestations include inhibition of Z A1AT polymerisation and increased clearance of polymers through the activation of autophagy. Investigational approaches to improved treatment of both the lung and the liver manifestations are directed towards improvement of Z A1AT folding and secretion.

Elliott et al (Protein Science, 2000, 9, 1274-1281) have described an X-ray crystal structure of A1AT and identified five cavities that are potential targets for rational drug design to develop agents that will affect Z A1AT polymerisation.

Parfrey et al (J. Biol. Chem., 2003, 278, 35, 33060-33066) have further defined a single cavity that is a potential target for rational drug design to develop agents that will affect Z A1AT polymerisation.

Knaupp et al (J. Mol. Biol., 2010, 396, 375-383) have shown that bis-ANS (4,4'-dianilino-1,1'-binaphthyl-5,5'-disulfonate) is able to bind to Z A1AT but not to wild-type A1AT (M) with 1:1 stoichiometry and a $K_d$ of 700 nM.

Chang et al (J. Cell. Mol. Med., 2009, 13, 8B, 2304-2316) have reported a series of peptides, including Ac-TTAI-$NH_2$, that inhibit Z A1AT polymerization.

Burrows et al (Proc. Nat. Acad. Sci., 2000, 97, 4, 1796-1801) have shown that a series of non-selective chaperones, including 4-phenylbutyric acid, glycerol and trimethylamine oxide, are able to increase Z A1AT levels in cell supernatants and mouse models.

Bouchecareilh et al. (Journal of Biological Chemistry, 2012, 287, 45, 38265-38278) describe the use of histone deacetylase inhibitors, in particular SAHA (suberoylanilide hydroxamic acid) to increase the secretion of both M and Z A1AT from cells.

Berthelier et al (PLOS ONE, May 11, 2015) have demonstrated that S-(4-nitrobenzyl)-6-thioguanosine is able to prevent Z A1AT polymerisation in vitro.

Mallya et al (J. Med. Chem., 2007, 50, 22, 5357-5363) describe a series of phenols, such as N-(4-hydroxy-3,5-dimethylphenyl)-2,5-dimethylthiophene-3-sulfonamide, able to block polymerisation of Z A1AT in vitro.

Huntington (XIIIth International Symposium on Proteinases, Inhibitors and Biological Control, 23 Sep. 2012, and $7^{th}$ International Symposium on Serpin Biology, Structure and Function, 1 Apr. 2014) discussed a cavity from an X-ray crystal structure of Z A1AT that is a potential target for rational drug design to develop agents that will affect Z A1AT polymerisation.

U.S. Pat. No. 8,436,013B2 discloses a wide variety of structures able to increase secretion of Z A1AT from cells in the micromolar range.

Angewandte Chemie International Edition vol 56, no 33, 2017, 9881-9885 discloses 1-((4-chlorophenyl)sulfonyl)piperidine-4-carboxylic acid as a herbicide.

Journal of Applicable Chemistry vol 2, no 6, 2013, 1501-1508 discloses the synthesis of 1-(4-(trifluoromethyl) phenylsulfonyl)piperidine-4-carboxylic acid as an anti-bacterial agent.

US2011/0065707A1 discloses the use of 1-(2-chlorobenzene-sulfonyl)-piperidine-4-carboxylic acid as a reagent.

EP0520336A2 discloses 1-(8-quinoyl-sulfonyl)-piperidine-4-carboxylic acid.

WO2019/243841A1 discloses oxoindoline-4-carboxamide compounds as modulators of alpha-1-antitrypsin, and use in treating diseases associated with alpha-1-antitrypsin.

WO2020/081257A1 discloses pyrrolo-indazolyl-propanoic acid compounds as modulators of alpha-1-antitrypsin.

US2020/0361939A1 discloses further pyrrolo-indazolyl-propanoic acid compounds as modulators of alpha-1-antitrypsin.

A prior art search based on the structure of 1-((2-(trifluoromethyl)phenyl)sulfonyl)piperidine-3-carboxylic acid was conducted after the invention was made. The closest prior art molecule identified ex post facto by the search was the racemic compound, 1-((2-(trifluoromethyl)phenyl)sulfonyl) piperidine-3-carboxylic acid (CAS registry number 891392-68-0). This compound is listed as commercially available from Aurora, ChemDiv and the FCH Group but no publications are recorded. Another close prior art molecule is 1-(1-tosyl-1,2,5,6-tetrahydropyridin-3-yl)ethan-1-one (Example 16 in U.S. Pat. No. 9,084,782B2). The compound is stated to inhibit angiogenesis and lower cellular cholesterol levels (although no biological data are provided for this compound in U.S. Pat. No. 9,084,782B2).

According to a first aspect of the present invention, there is provided a pharmaceutical composition comprising the compound (S)-1-((2-(trifluoromethyl)phenyl)sulfonyl)piperidine-3-carboxylic acid

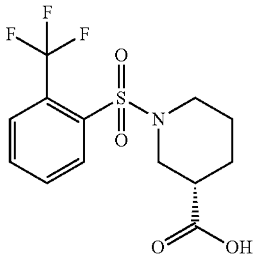 [SMILES: O=C(O)[C@H]1CCCN(S(=O)(=O)c2ccccc2C(F)(F)F)C1]

for use in treating a disease or disorder characterised by low plasma levels of A1AT in a human subject, wherein the composition is administered to the human subject at a daily dose of about 1-6 mg/kg (i.e. about 1-6 mg of pharmaceutical composition per mass of the human subject in kg).

The composition may be administered to the human subject at a daily dose of about 2-5 mg/kg, or for example about 1 mg/kg, about 1.5 mg/kg, about 2 mg/kg, about 2.5 mg/kg about 3 mg/kg, about 3.5 mg/kg, about 4 mg/kg, about 4.5 mg/kg, about 5 mg/kg, about 5.5 mg/kg, or about 6 mg/kg.

In other aspects of the invention, the composition may be administered to the human subject at different intervals, for example every second, third, fourth, fifth or sixth day, or weekly, at a dose equivalent to the daily dose specified herein.

As elaborated below, we have found that (S)-1-((2-(trifluoromethyl)phenyl)sulfonyl)piperidine-3-carboxylic acid is surprisingly highly effective at increasing levels of Z A1AT, both in vitro and in vivo, whilst having no effect on the in vitro secretion of M A1AT or of the Siiyama variant of A1AT.

Furthermore, as shown in Examples 7, 8 and 14, (S)-1-((2-(trifluoromethyl)phenyl)sulfonyl)piperidine-3-carboxylic acid exhibits pharmacokinetic properties which indicates that it will be effective for treating AATD at a surprisingly much lower dose than its enantiomer (R)-1-((2-(trifluoromethyl)phenyl)sulfonyl)piperidine-3-carboxylic acid:

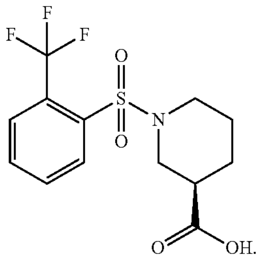 [SMILES: O=C(O)[C@@H]1CCCN(S(=O)(=O)c2ccccc2C(F)(F)F)C1]

The compound in the pharmaceutical composition of the invention may be in a pharmaceutically acceptable salt form.

The term "pharmaceutically acceptable salt" refers to a pharmaceutically acceptable mono organic or inorganic salt of the compound of the invention. This may include those derived from bases such as sodium hydroxide, potassium hydroxide, lithium hydroxide, calcium hydroxide, 1-deoxy-2-(methylamino)-D-glucitol, magnesium hydroxide, zinc hydroxide, aluminium hydroxide, ferrous or ferric hydroxide, ammonium hydroxide or organic amines such as N-methylglucamine, choline, arginine and the like. For other examples of pharmaceutically acceptable salts, reference can be made to Gould (1986, Int J Pharm 33: 201-217).

The pharmaceutical composition of the invention may further comprise a pharmaceutically or therapeutically acceptable excipient or carrier.

The term "pharmaceutically or therapeutically acceptable excipient or carrier" refers to a solid or liquid filler, diluent or encapsulating substance which does not interfere with the effectiveness or the biological activity of the active ingredients and which is not toxic to the host, which may be either humans or animals, to which it is administered. Depending upon the particular route of administration, a variety of pharmaceutically acceptable carriers such as those well known in the art may be used. Non-limiting examples include sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

All suitable modes of administration are contemplated according to the invention. For example, administration of the composition or medicament may be via oral, subcutaneous, direct intravenous, slow intravenous infusion, continuous intravenous infusion, intravenous or epidural patient controlled analgesia (PCA and PCEA), intramuscular, intrathecal, epidural, intracistemal, intraperitoneal, transdermal, topical, transmucosal, buccal, sublingual, transmucosal, inhalation, intranasal, intra-atricular, intranasal, rectal or ocular routes. The composition or medicament may be formulated in discrete dosage units (for example, as required by the daily dosage regime of the invention) and can be prepared by any of the methods well known in the art of pharmacy.

The composition may in particular be administered in oral form. Alternatively, the composition may be administered intravenously.

All suitable pharmaceutical dosage forms are contemplated. Administration of the medicament may for example be in the form of oral solutions and suspensions, tablets, capsules, lozenges, effervescent tablets, transmucosal films, suppositories, buccal products, oral mucoretentive products, topical creams, ointments, gels, films and patches, transdermal patches, abuse deterrent and abuse resistant formulations, sterile solutions suspensions and depots for parenteral use, and the like, administered as immediate release, sustained release, delayed release, controlled release, extended release and the like.

Another aspect of the invention is the use of (S)-1-((2-(trifluoromethyl)phenyl)sulfonyl)piperidine-3-carboxylic acid in the manufacture of a medicament for the treatment of a disease or disorder characterised by low plasma levels of A1AT in a human subject, wherein the medicament is administered to the human subject at a daily dose of about 1-6 mg/kg (including in doses as recited above).

The invention also encompasses a method of treating a disease or disorder characterised by low plasma levels of A1AT in a human subject, comprising the step of administering a pharmaceutical composition as defined herein comprising (S)-1-((2-(trifluoromethyl)phenyl)sulfonyl)piperidine-3-carboxylic acid at a daily dose of about 1-6 mg/kg (including in doses as recited above).

A disease or disorder suitable for treatment according to the relevant aspects of the invention is one which is characterised by low plasma levels of A1AT, for example $\alpha_1$-antitrypsin deficiency (AATD).

The use of a numerical range in this description is intended unambiguously to include within the scope of the invention all individual integers within the range and all the combinations of upper and lower limit numbers within the broadest scope of the given range.

As used herein, the term "comprising" is to be read as meaning both comprising and consisting of. Consequently, where the invention relates to a "pharmaceutical composition comprising as active ingredient" a compound, this terminology is intended to cover both compositions in which other active ingredients may be present and also compositions which consist only of one active ingredient as defined.

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference in their entirety (where legally permissible).

Figure 2:
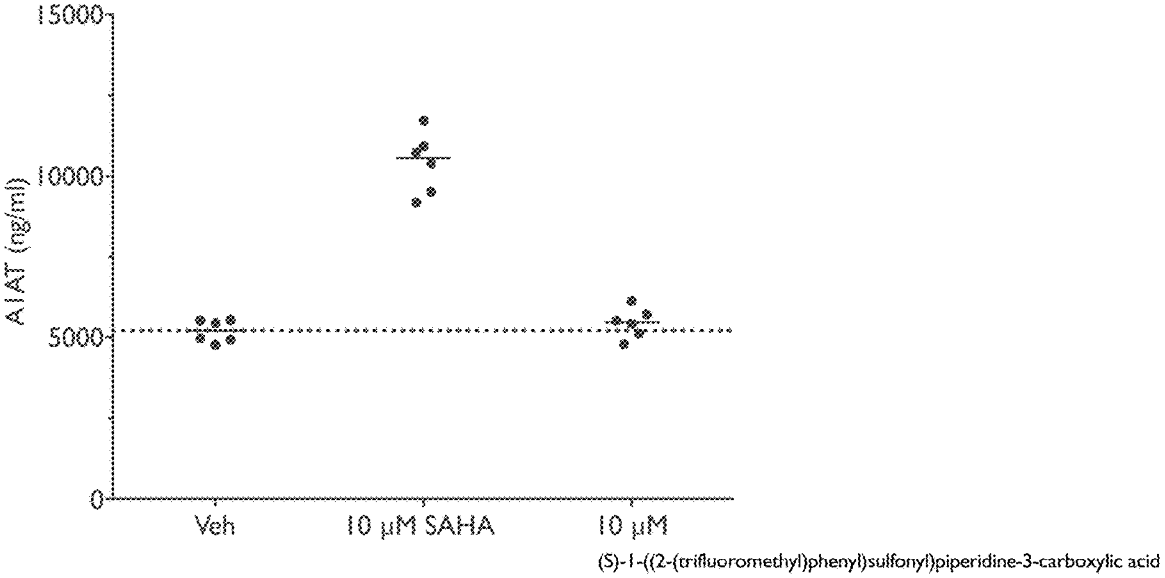
Figure 3:
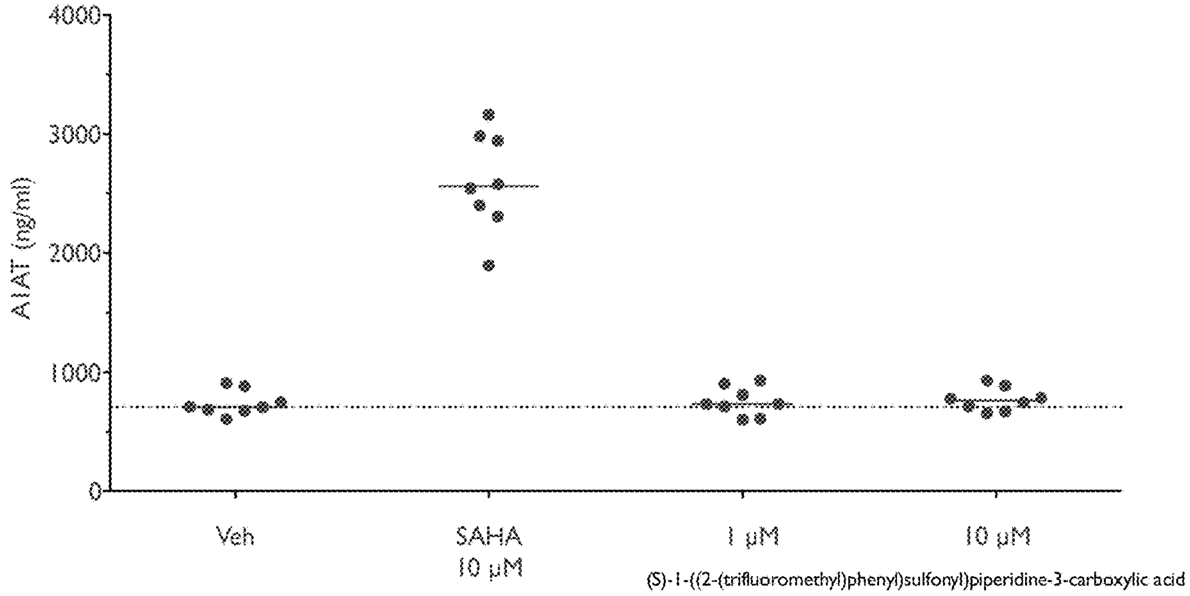
Figure 4:
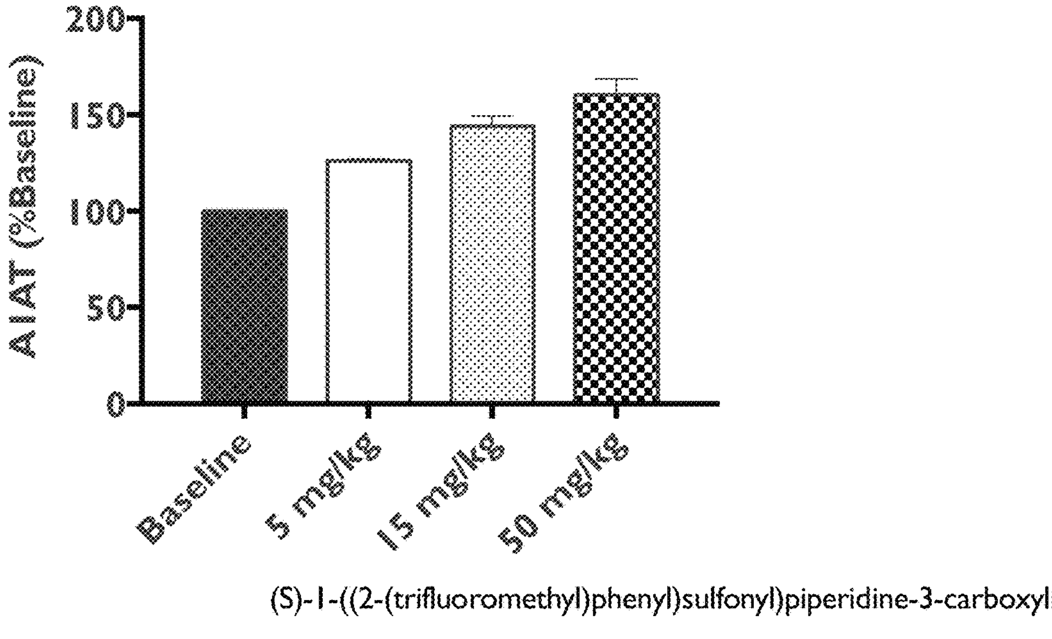

Particular non-limiting examples of the present invention will now be described with reference to the following drawings, in which:

FIG. 1 is a graph showing the dose dependent effect of (S)-1-((2-(trifluoromethyl)phenyl)sulfonyl)piperidine-3-carboxylic acid in an in vitro A1AT cell secretion assay using HEK-EBNA cells containing the Z A1AT plasmid. Vehicle and 10 μM SAHA were tested on each plate as controls. The x-axis shows various treatments of the cells: vehicle, SAHA and increasing concentrations of (S)-1-((2-(trifluoromethyl)phenyl)sulfonyl)piperidine-3-carboxylic acid, the y-axis is the concentration of human A1AT in the cell supernatant (in ng/ml):

FIG. 2 is a graph showing the effect of (S)-1-((2-(trifluoromethyl)phenyl)sulfonyl)piperidine-3-carboxylic acid at 10 μM in an in vitro A1AT cell secretion assay using HEK-EBNA cells containing M A1AT plasmid. Vehicle and 10 μM SAHA were tested as controls. The x-axis shows various treatments of the cells: vehicle, SAHA and (S)-1-((2-(trifluoromethyl)phenyl)sulfonyl)piperidine-3-carboxylic acid, the y-axis is the concentration of human A1AT in the cell supernatant (in ng/ml):

FIG. 3 is a graph showing the effect of (S)-1-((2-(trifluoromethyl)phenyl)sulfonyl)piperidine-3-carboxylic acid at 1 and 10 μM in an in vitro A1AT cell secretion assay using HEK-EBNA cells containing the Siiyama A1AT plasmid. Vehicle and 10 μM SAHA were tested as controls. The x-axis shows various treatments of the cells: vehicle, SAHA and two concentrations of (S)-1-((2-(trifluoromethyl)phenyl)sulfonyl)piperidine-3-carboxylic acid, the y-axis is the concentration of human A1AT in the cell supernatant (in ng/ml);

FIG. 4 is a graph showing the effect of (S)-1-((2-(trifluoromethyl)phenyl)sulfonyl)piperidine-3-carboxylic acid on Z A1AT levels in mice expressing human Z A1AT (huZ mice). Mice were treated with vehicle, 5, 15 and 50 mg/kg of (S)-1-((2-(trifluoromethyl)phenyl)sulfonyl)piperidine-3-carboxylic acid twice a day by oral gavage for 14 consecutive days. Blood was taken on days −12, −7 and −5 and plasma prepared to determine circulating basal levels of human Z A1AT. Plasma samples collected the last three days of the study (days 12, 13 and 14) were used to determine the effect of (S)-1-((2-(trifluoromethyl)phenyl)sulfonyl)piperidine-3-carboxylic acid treatment on circulating human Z A1AT levels compared to basal levels. The x-axis is the treatment dose of (S)-1-((2-(trifluoromethyl)phenyl)sulfonyl)piperidine-3-carboxylic acid in mg/kg: the y-axis is the mean percentage level of human Z A1AT compared to baseline levels for each treatment group.

Figure 5:
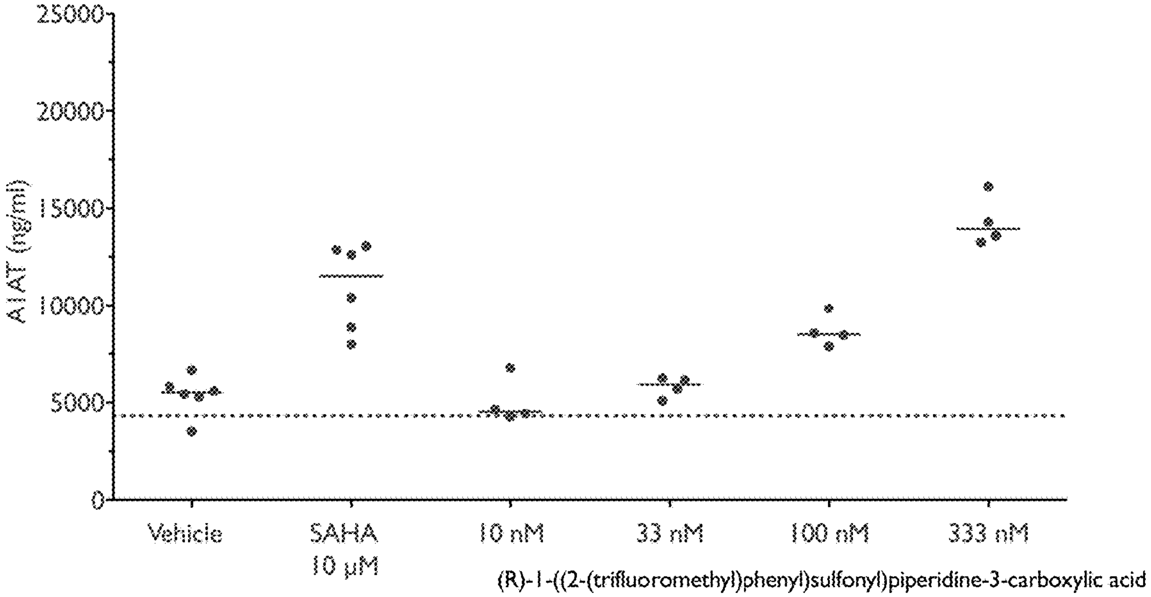
Figure 6:
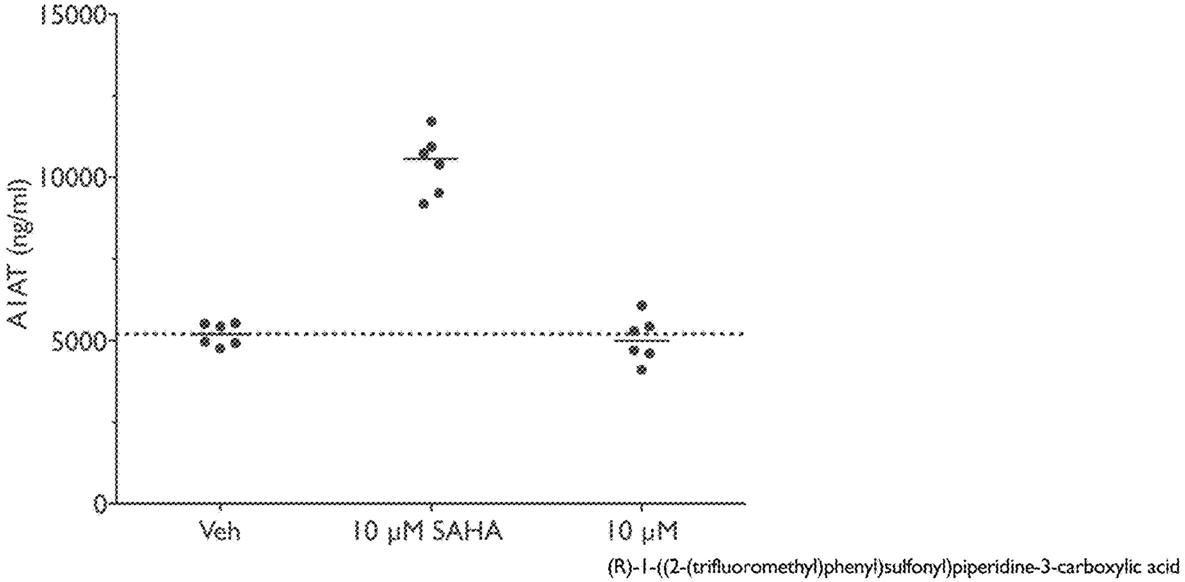
Figure 7:
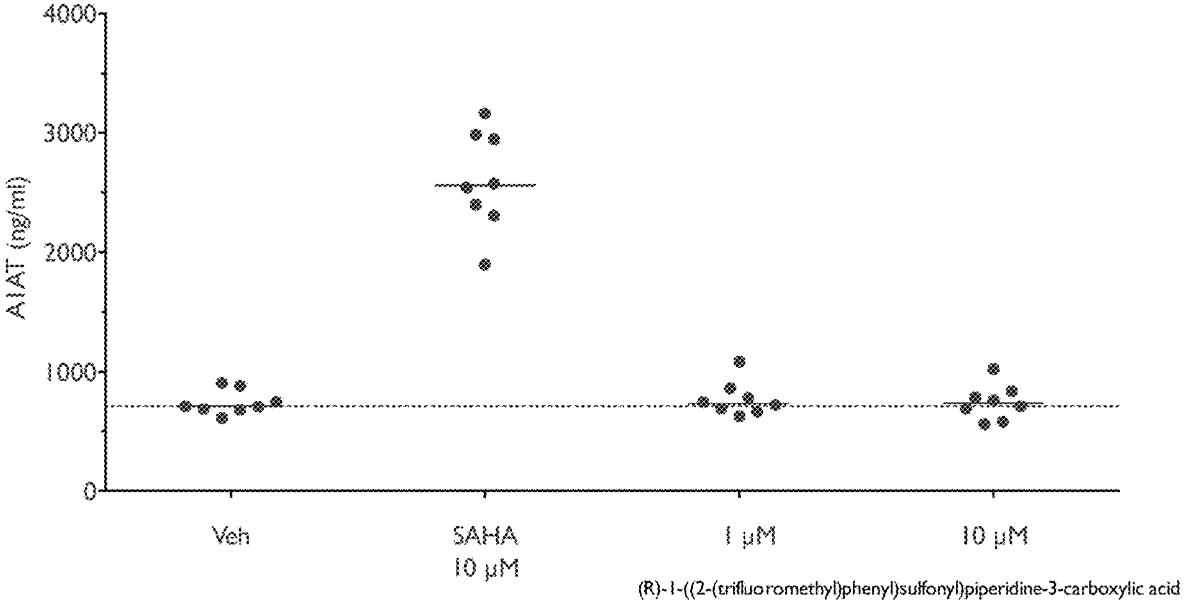

FIG. 5 is a graph showing the dose dependent effect of (R)-1-((2-(trifluoromethyl)phenyl)sulfonyl)piperidine-3-carboxylic acid in an in vitro A1AT cell secretion assay using HEK-EBNA cells containing the Z A1AT plasmid. Vehicle and 10 μM SAHA were tested on each plate as controls. The x-axis shows various treatments of the cells: vehicle, SAHA and increasing concentrations of (R)-1-((2-(trifluoromethyl)phenyl)sulfonyl)piperidine-3-carboxylic acid, the y-axis is the concentration of human A1AT in the cell supernatant (in ng/ml);

FIG. 6 is a graph showing the effect of (R)-1-((2-(trifluoromethyl)phenyl)sulfonyl)piperidine-3-carboxylic acid at 10 μM in an in vitro A1AT cell secretion assay using HEK-EBNA cells containing the M A1AT plasmid. Vehicle and 10 μM SAHA were tested as controls. The x-axis shows various treatments of the cells: vehicle, SAHA and (R)-1-((2-(trifluoromethyl)phenyl)sulfonyl)piperidine-3-carboxylic acid, the y-axis is the concentration of human A1AT in the cell supernatant (in ng/ml); and FIG. 7 is a graph showing the effect of (R)-1-((2-(trifluoromethyl)phenyl)sulfonyl)piperidine-3-carboxylic acid at 1 and 10 μM in an in vitro A1AT cell secretion assay using HEK-EBNA cells containing the Siiyama A1AT plasmid. Vehicle and 10 μM SAHA were tested as controls. The x-axis shows various treatments of the cells: vehicle, SAHA and two concentrations of (S)-1-((2-(trifluoromethyl)phenyl)sulfonyl)piperidine-3-carboxylic acid, the y-axis is the concentration of human A1AT in the cell supernatant (in ng/ml).

EXPERIMENTAL

Example 1: (S)-1-((2-(Trifluoromethyl)phenyl)sulfonyl)piperidine-3-carboxylic acid (S)-1-((2-(Trifluoromethyl)phenyl)sulfonyl)piperidine-3-carboxylic acid was prepared using the following synthesis procedure.

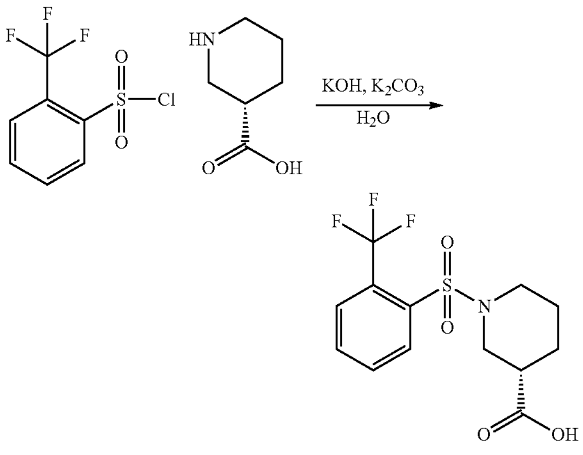

(S)-Piperidine-3-carboxylic acid (1 g, 7.7 mmol), potassium hydroxide (434 mg, 7.7 mmol) and potassium carbonate (2.14 g, 15.4 mmol) were added to water (20 ml) and stirred. 2-(Trifluoromethyl)benzenesulfonyl chloride (1.89 g, 7.7 mmol) was added and the reaction was stirred at room temperature for 3 hours. The reaction was cooled to 0° C. and acidified with 2M hydrochloric acid to give a white precipitate. This precipitate was dried and triturated with n-pentane to give (S)-1-((2-(trifluoromethyl)phenyl)sulfonyl)piperidine-3-carboxylic acid.

Tlc Rf 0.3 70% ethyl acetate in hexane.

m/z: 337.98 (calc 338.03)

$^1$H NMR (400 MHZ, d6 DMSO) δ 12.33 (1H, s), 8.04 (2H, m), 7.90 (2H, m), 3.69 (1H, dd), 3.50 (1H, dd), 2.93 (1H, m), 2.81 (1H, m), 1.91 (1H, m), 1.72 (1H, m), 1.50 (2H, m).

Example 2: (R)-1-((2-(Trifluoromethyl)phenyl)sulfonyl)piperidine-3-carboxylic acid (R)-1-((2-(Trifluoromethyl)phenyl)sulfonyl)piperidine-3-carboxylic acid was prepared in the same manner as (S)-1-((2-(trifluoromethyl)phenyl)sulfonyl)piperidine-3-carboxylic acid, but using (R)-piperidine-3-carboxylic acid.

Tlc Rf 0.3 70% ethyl acetate in hexane.

m/z: 338.03 (calc 338.03)

$^1$H NMR (400 MHZ, d6 DMSO) δ 12.53 (1H, s), 8.04 (2H, m), 7.90 (2H, m), 3.69 (1H, dd), 3.49 (1H, dd), 2.93 (1H, m), 2.81 (1H, m), 1.90 (1H, m), 1.72 (1H, m), 1.49 (2H, m).

Example 3: Activity of (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid in an A1AT cell secretion assay using HEK-Z cells Methods HEK-Z cells, a human embryonic kidney cell line stably transfected with the human Z A1AT gene, were plated into 96 well plates ($3.0\times10^5$ cells/ml with 200 µl of media/well) overnight at 37° C. in a humidified atmosphere containing 5% $CO_2$. Following incubation cells were washed with 200 µl serum-free media three times and media was replaced with treatments in quadruplicate using serum-free media containing vehicle, 10 µM suberanilohydroxamic acid (SAHA), (S)-1-((2-(trifluoromethyl)phenyl)sulfonyl)piperidine-3-carboxylic acid or (R)-1-((2-(trifluoromethyl)phenyl)sulfonyl)piperidine-3-carboxylic acid (at concentrations of 10, 33, 100 and 333 nM) for 48 h in a 37° C. incubator in a final volume of 200 µl. At the end of the incubation step the supernatants were removed from the wells, centrifuged at 1000×g at 4° C. for 10 min and were assayed for human A1AT levels by ELISA (Human Serpin A1/$\alpha_1$-antitrypsin duo set ELISA, R& D Systems, DY1268) per manufacturer's instructions.

Briefly, a 96 well plate was coated with human A1AT capture antibody overnight at room temperature (1:180 dilution from stock, 100 µl final volume/well). The capture antibody was then removed and wells washed three times with 300 µl wash buffer (0.05% Tween 20 in PBS) and then 200 µl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 µl detection antibody (1:180 dilution from stock) was added to each well and incubated for a further 2 h at room temperature. Following incubation with detection antibody, supernatant was removed and wells were washed as previously and 100 µl streptavidin-HRP solution (1:200 dilution from stock) was added to each well for 20 min in the dark. After which, 50 µl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The amount of human A1AT secreted from transfected HEK-EBNA cells into the media was measured by ELISA. SAHA at 10 µM was used a positive control for all in vitro A1AT secretion experiments.

The data in FIG. 1 show that (S)-1-((2-(trifluoromethyl)phenyl)sulfonyl)piperidine-3-carboxylic acid stimulates secretion of human Z A1AT in a dose dependent manner as measured by ELISA.

The data in FIG. 5 show that (R)-1-((2-(trifluoromethyl)phenyl)sulfonyl)piperidine-3-carboxylic acid stimulates secretion of human Z A1AT in a dose dependent manner as measured by ELISA.

Example 4: Activity of (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid in an A1AT cell secretion assay using HEK-M cells Methods HEK-M cells, a human embryonic kidney cell line stably transfected with M A1AT, were plated into 96 well plates ($3.0\times10^5$ cells/ml with 200 µl of media/well) overnight at 37° C. in a humidified atmosphere containing 5% $CO_2$. Following incubation cells were washed with 200 µl serum-free media three times and media was replaced with serum-free media containing either vehicle, 10 µM suberanilohydroxamic acid (SAHA), (S)-1-((2-(trifluoromethyl)phenyl)sulfonyl)piperidine-3-carboxylic acid (at 10 µM) or (R)-1-((2-(trifluoromethyl)phenyl)sulfonyl)piperidine-3-carboxylic acid (at 10 µM) in replicates of six for 48 h in a 37° C. incubator in a final volume of 200 µl. At the end of the incubation step the supernatants were removed from the wells, centrifuged at 1000×g at 4° C. for 10 min and were assayed for human A1AT levels by ELISA (Human Serpin A1/$\alpha_1$ antitrypsin duo set ELISA, R& D Systems, DY1268) per manufacturer's instructions.

Briefly, a 96 well plate was coated with human A1AT capture antibody overnight at room temperature (1:180 dilution from stock, 100 µl final volume/well). The capture antibody was then removed and wells washed three times with 300 µl wash buffer (0.05% Tween in PBS) and then 200 µl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 µl detection antibody (1:180 dilution from stock) was added to each well and incubated for a further 2 h at room temperature. Following incubation with detection antibody, supernatant was removed and wells were washed as previously and 100 µl streptavidin-HRP solution (1:200 dilution from stock) was added to each well for 20 min in the dark. After which, 50 µl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The amount of human A1AT secreted from transfected HEK-EBNA cells into the media was measured by ELISA. SAHA at 10 μM was used a positive control for all in vitro A1AT secretion experiments.

The data in FIG. 2 show that (S)-1-((2-(trifluoromethyl)phenyl)sulfonyl)piperidine-3-carboxylic acid does not stimulate secretion of human M A1AT at 10 μM, as measured by ELISA. In contrast, the positive control 10 μM SAHA stimulates an increase in M A1AT secretion.

The data in FIG. 6 show that (R)-1-((2-(trifluoromethyl)phenyl)sulfonyl)piperidine-3-carboxylic acid does not stimulate secretion of human M A1AT at 10 μM, as measured by ELISA. In contrast, the positive control 10 μM SAHA stimulates an increase in M A1AT secretion.

Example 5: Activity of (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid in an A1AT cell secretion assay using HEK-Siiyama cells The rare Siiyama mutation (Ser 53 to Phe, mature A1AT numbering) was identified in a Japanese male with AATD (Seyama et al (J Biol Chem (1991) 266:12627-32). Ser53 is one the conserved serpin residues and is thought to be important for the organization of the internal core of the A1AT molecule. The change from an uncharged polar to a large nonpolar amino acid on the conserved backbone of the protein affects the folding and intracellular processing of Siiyama A1AT.

Methods

HEK-Siiyama cells, a human embryonic kidney cell line stably transfected with the Siiyama A1AT gene, were plated into 96 well plates ($3.0\times10^5$ cells/ml with 200 μl of media/well) overnight at 37° C. in a humidified atmosphere containing 5% $CO_2$. Following incubation cells were washed with 200 μl serum-free media three times and media was replaced with serum-free media containing vehicle, 10 μM suberanilohydroxamic acid (SAHA), (S)-1-((2-(trifluoromethyl)phenyl)sulfonyl)piperidine-3-carboxylic acid (at 1 or 10 μM) or (R)-1-((2-(trifluoromethyl)phenyl)sulfonyl)piperidine-3-carboxylic acid (at 1 or 10 μM) in replicates of eight for 48 h in a 37° C. incubator in a final volume of 200 μl. At the end of the incubation step the supernatants were removed from the wells, centrifuged at 1000×g at 4° C. for 10 min and were assayed for human A1AT levels by ELISA (Human Serpin A1/$\alpha_1$-antitrypsin duo set ELISA, R& D Systems, DY1268) per manufacturer's instructions.

Briefly, a 96 well plate was coated with human A1AT capture antibody overnight at room temperature (1:180 dilution from stock, 100 μl final volume/well). The capture antibody was then removed and wells washed three times with 300 μl wash buffer (0.05% Tween 20 in PBS) and then 200 μl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 μl detection antibody (1:180 dilution from stock) was added to each well and incubated for a further 2 h at room temperature. Following incubation with detection antibody, supernatant was removed and wells were washed as previously and 100 μl streptavidin-HRP solution (1:200 dilution from stock) was added to each well for 20 min in the dark. After which, 50 μl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The amount of human A1AT secreted from transfected HEK-EBNA cells into the media was measured by ELISA. SAHA at 10 μM was used a positive control for all in vitro A1AT secretion experiments.

The data in FIG. 3 show that (S)-1-((2-(trifluoromethyl)phenyl)sulfonyl)piperidine-3-carboxylic acid does not stimulate secretion of human Siiyama A1AT at 1 or 10 μM, as measured by ELISA. In contrast, the positive control 10 μM SAHA stimulates an increase in Siiyama A1AT secretion.

The data in FIG. 7 show that (R)-1-((2-(trifluoromethyl)phenyl)sulfonyl)piperidine-3-carboxylic acid does not stimulate secretion of human Siiyama A1AT at 1 or 10 μM, as measured by ELISA. In contrast, the positive control 10 μM SAHA stimulates an increase in Siiyama A1AT secretion.

Example 6: Activity of (S)-1-((2-(trifluoromethyl)phenyl)sulfonyl)piperidine-3-carboxylic acid in huZ mice The huZ mouse (also referred to as the PiZZ mouse) is a transgenic mouse strain that contains multiple copies of the Z variant of the human A1AT gene, developed by two separate groups (Dycaico et al (Science (1988) 242:1409-12) and Carlson et al (J. Clin Invest (1989) 83:1183-90)). HuZ mice are on a C57Bl/6 background and express the human Z A1AT protein in liver tissue. The mice used in this study are from the progeny of Carlson and colleagues (transgenic line Z11.03). HuZ mice have been used as a tool to assess the effects of compounds on either increasing the circulating levels of Z A1AT in plasma or the effects of compounds on the accumulation of Z A1AT polymers in the liver and associated liver pathology.

HuZ mice (n=4/group: male or female) with basal human A1AT plasma levels of between 200-600 μg/ml were treated with either vehicle or (S)-1-((2-(trifluoromethyl)phenyl)sulfonyl)piperidine-3-carboxylic acid at 5, 15 or 50 mg/kg twice a day by oral gavage for 14 consecutive days. Mice had access to food (standard mouse chow, SAFE diets) and water ad libitum. On study day 14, each mouse was dosed one hour prior to terminal procedures. Blood was taken from each mouse from the tail vein on pre-dosing days −12, −7 and −5 and dosing days 12, 13 and 14. Blood was collected into microvettes containing EDTA and plasma was prepared by centrifugation at 2700×g at 4° C. for 10 min. Plasma was aliquoted and stored at −80° C. for bioanalysis. Plasma samples from pre-dosing days −12, −7 and −5 were used to determine mean basal levels of human Z A1AT for each mouse. Plasma samples collected on the last three dosing days of the study (days 12, 13 and 14) were used to determine the effect of (S)-1-((2-(trifluoromethyl)phenyl)sulfonyl)piperidine-3-carboxylic acid on human Z A1AT secretion by measuring human Z A1AT levels and comparing to basal levels for each mouse. Human A1AT levels in mouse plasma samples were measured by ELISA (Human Serpin A1/$\alpha_1$ antitrypsin duo set ELISA, R& D Systems, DY1268) per manufacturer's instructions.

Briefly, a 96 well plate was coated with human A1AT capture antibody overnight at room temperature (1:180 dilution from stock, 100 μl final volume/well). The capture antibody was then removed and wells washed three times with 300 μl wash buffer (0.05% Tween 20 in PBS) and then 200 μl reagent diluent (25% Tween 20 in PBS) was incubated in each well for 1 h at room temperature. Diluted samples, standards (125, 250, 500, 1000, 2000, 4000 and 8000 pg/ml A1AT) or blanks were then added to each well in duplicate and the plates were covered with a plate sealer and left at room temperature for 2 h. At the end of the sample incubation step, samples were removed and all wells washed as previously and 100 μl detection antibody (1:180 dilution from stock) was added to each well and incubated for a further 2 h at room temperature. Following incubation with detection antibody, supernatant was removed and wells were washed as previously and 100 μl streptavidin-HRP solution (1:200 dilution from stock) was added to each well for 20 min in the dark. After which, 50 μl stop solution (2M $H_2SO_4$) was added and optical density (OD) of each well was read at 450 nm with 570 nm blank subtracted from each well using a microplate reader. A 4 parameter logistic curve was constructed using GraphPad Prism 7 and A1AT concentrations were determined in each sample by interpolation from a standard curve and multiplying by the appropriate dilution factor.

Results

The effect of (S)-1-((2-(trifluoromethyl)phenyl)sulfonyl)piperidine-3-carboxylic acid on circulating levels of human Z A1AT was assessed in a huZ mouse model. Mice were treated for 14 consecutive days by oral gavage twice daily at 5, 15 or 50 mg/kg.

The data in FIG. 4 show that (S)-1-((2-(trifluoromethyl)phenyl)sulfonyl)piperidine-3-carboxylic acid stimulates secretion of human Z A1AT compared to baseline levels in huZ mice in a dose dependent manner.

Example 7: Pharmacokinetics of (S)-1-((2-(trifluoromethyl)phenyl)sulfonyl)piperidine-3-carboxylic acid in mice (S)-1-((2-(trifluoromethyl)phenyl)sulfonyl)piperidine-3-carboxylic acid was administered to male C57BI/6 mice intravenously (2 mg/kg) or orally (10 mg/kg) by gavage. Whole blood diluted with water was prepared from these dosed animals over a time course up to 24 hours post dose to allow blood concentrations of drug to be measured by UPLC-MS/MS. The measured drug levels allowed calculation of the following parameters for (S)-1-((2-(trifluoromethyl)phenyl)sulfonyl)piperidine-3-carboxylic acid.

Half-life in blood ($t_{1/2}$)=1.2 h

Observed clearance=4.7 ml/min/kg

Volume of distribution (Vz)=0.49 l/kg

Oral $C_{max}$=33520 ng/ml $AUC_{all}$=54234 ng·h/ml $AUC_{INF}$=54372 ng·h/ml

Example 8: Pharmacokinetics of (R)-1-((2-(trifluoromethyl)phenyl)sulfonyl)piperidine-3-carboxylic acid in mice (R)-1-((2-(trifluoromethyl)phenyl)sulfonyl)piperidine-3-carboxylic acid was administered to male C57BI/6 mice intravenously (2 mg/kg) or orally (10 mg/kg) by gavage. Whole blood diluted with water was prepared from these dosed animals over a time course up to 24 hours post dose to allow blood concentrations of drug to be measured by UPLC-MS/MS. The measured drug levels allowed calculation of the following parameters for (R)-1-((2-(trifluoromethyl)phenyl)sulfonyl)piperidine-3-carboxylic acid.

Half-life in blood ($t_{1/2}$)=0.54 h

Observed clearance=8.2 ml/min/kg

Volume of distribution (Vz)=0.38 l/kg

Oral Cmax=15599 ng/ml

AUCall=24158 ng·h/ml

AUCINF=24736 ng·h/ml

Example 9: Mouse and human hepatocyte stability of (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid The intrinsic clearance ($CL_{int}$) and half-life of (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid were measured in a hepatocyte suspension of cryopreserved male C57BL6 mouse hepatocytes or a mixed hepatocyte suspension of cryopreserved human hepatocytes. Briefly, the compounds were incubated with hepatocyte suspensions at 37° C. over a time course and the remaining compound at each time point was assessed by mass spectrometry (UPLC-MS/MS). $CL_{int}$ in mouse hepatocytes was <3 μl/min/$10^6$ cells and in human hepatocytes was <3 μl/min/$10^6$ cells for both compounds. The half-life in mouse hepatocytes was >460 min and in human hepatocytes was >460 min for both compounds.

Example 10: Plasma Protein Binding of (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid The extent to which (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid bound to plasma proteins such as albumin and alpha-1 acid glycoprotein within human or mouse blood was determined by rapid equilibrium dialysis. Compounds were incubated at 5 μM for 4 hours at 37° C. Plasma protein binding in mouse plasma was 78.1% and in human plasma was 91.5% for (S)-1-((2-(trifluoromethyl)phenyl)sulfonyl)piperidine-3-carboxylic acid. Plasma protein binding in mouse plasma was 83.8% and in human plasma was 90.5% for (R)-1-((2-(trifluoromethyl)phenyl)sulfonyl)piperidine-3-carboxylic acid.

Example 11: Activity of (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid against cytochrome P450s Using *E. coli* CYPEX membranes in combination with specific probe substrates, the inhibition of individual CYPs by (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid was assessed (see Weaver et al., 2003, Drug Metab Dispos 31:7, 955-966).

TABLE 1

| In vitro PK drug-drug interactions | | | | | |
|---|---|---|---|---|---|
| | CYP Inhibition (IC50 - μM) | | | | |
| | 1A2 | 2C9 | 2C19 | 2D6 | 3A4 |
| (S)-1-((2-(trifluoromethyl)phenyl)sulfonyl)piperidine-3-carboxylic acid | >50 | >50 | >50 | >50 | >50 |
| (R)-1-((2-(trifluoromethyl)phenyl)sulfonyl)piperidine-3-carboxylic acid | >50 | >50 | >50 | >50 | >50 |

Example 12: Activity of (S)-1-((2-(trifluoromethyl)phenyl)sulfonyl)piperidine-3-carboxylic acid against the HERG channel (S)-1-((2-(trifluoromethyl)phenyl)sulfonyl)piperidine-3-carboxylic acid was tested for inhibition of cardiac potassium (hERG) channels using the Patchliner automated patch clamp. 6-Point concentration-response curves were generated using half-log serial dilutions from a maximum final test concentration of 100 μM. $IC_{50}$ values were obtained from a 4-parameter logistic fit of the concentration-response data. (S)-1-((2-(trifluoromethyl)phenyl)sulfonyl)piperidine-3-carboxylic acid was shown to have an IC50>100 μM with 7% inhibition at 100 μM. Reference compound values were consistent with those presented in the literature (Elkins et al., 2013 J. Pharm. Tox. Meth. 68:11-122).

Example 13: Activity of (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid against a panel of enzymes, ion channels and receptors (S)-1-((2-(trifluoromethyl)phenyl)sulfonyl)piperidine-3-carboxylic acid and (R)-1-((2-(trifluoromethyl)phenyl)sulfonyl)piperidine-3-carboxylic acid exhibited exceptionally clean off target profiles when tested against the DiscoverX Safety47™ panel at 10 μM. No target was inhibited by more than 25% at this concentration for either compound.

Example 14: Determining Human Equivalent Dose

The highest dose of (S)-1-((2-(trifluoromethyl)phenyl)sulfonyl)piperidine-3-carboxylic acid in mice used in efficacy studies to date is 50 mg/kg (data not shown). Converting this to a human equivalent dose using Table 1 of the US FDA Center for Drug Evaluation and Research (CDER) "Guidance for Industry: Estimating the Maximum Safe Starting Dose in Initial Clinical Trials for Therapeutics in Adult Healthy Volunteers" (2005 publication—see https://www.fda.gov/media/72309/download), a human equivalent dose (HED) of 4 mg/kg is indicated.

By comparison, as shown in Examples 7 and 8, the enantiomer (R)-1-((2-(trifluoromethyl)phenyl)sulfonyl)piperidine-3-carboxylic acid has a t½ that is 2.2 fold shorter and an AUC that is 2.2 fold lower in mice. In the expectation that clinical efficacy is driven either by AUC or time above a given concentration, we conclude that equivalent efficacy of the R enantiomer will be at a dose that is 2.2 fold higher or 8.8 mg/kg compared with the S enantiomer.

What is claimed is:

1. A method of treating a disease or disorder characterised by low plasma levels of A1AT in a human subject, comprising the step of administering a pharmaceutical composition comprising(S)-1-((2-(trifluoromethyl)phenyl)sulfonyl)piperidine-3-carboxylic acid

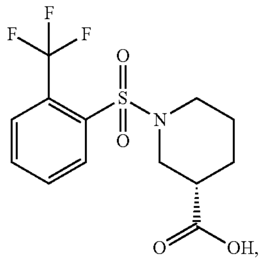 [SMILES: O=C(O)[C@H]1CCCN(S(=O)(=O)c2ccccc2C(F)(F)F)C1]

or a pharmaceutically acceptable salt form, and a pharmaceutically or therapeutically acceptable excipient or carrier, at a daily dose of about 1-6 mg/kg.

2. The method of claim 1, in which the disease or disorder is a1-antitrypsin deficiency (AATD).

3. The method of claim 1, wherein the administering to the human subject is at a daily dose of about 2-5 mg/kg.

4. The method of claim 3, wherein the daily dose is about 2 mg/kg.

5. The method of claim 3, wherein the daily dose is about 3 mg/kg.

6. The method of claim 3, wherein the daily dose is about 4 mg/kg.

7. The method of claim 3, wherein the daily dose is about 5 mg/kg.

8. The method of claim 1, wherein the composition is administered in oral form.

9. The method of claim 1, wherein the composition is administered intravenously.

* * * * *